United States Patent [19]

Yoldas

[11] 4,293,593

[45] Oct. 6, 1981

[54] METHOD OF FABRICATING HEAT MIRROR FOR INCANDESCENT LAMP ENVELOPE

[75] Inventor: Bulent E. Yoldas, Churchill, Pa.

[73] Assignee: Westinghouse Electric Corp., Pittsburgh, Pa.

[21] Appl. No.: 84,217

[22] Filed: Oct. 12, 1979

Related U.S. Application Data

[63] Continuation-in-part of Ser. No. 931,346, Aug. 8, 1978, abandoned.

[51] Int. Cl.$^3$ .................. C03C 17/36; G02B 1/10; H01K 1/32
[52] U.S. Cl. ............................ 427/106; 427/107; 427/160
[58] Field of Search ................. 427/106, 107, 160

[56] References Cited

U.S. PATENT DOCUMENTS

| | | | |
|---|---|---|---|
| 2,689,858 | 9/1954 | Boyd | 260/429 |
| 2,768,909 | 10/1956 | Haslam | 428/336 |
| 3,094,436 | 6/1963 | Schroder | 428/333 |
| 3,460,956 | 8/1969 | Dahle | 260/429 X |
| 4,017,758 | 4/1977 | Almer et al. | 313/112 |
| 4,160,929 | 7/1979 | Thorington et al. | 313/112 |

FOREIGN PATENT DOCUMENTS 703127  1/1954  United Kingdom .

OTHER PUBLICATIONS

Fan, "Wavelength-Selective Surfaces for Solar Energy Utilization", *Optics in Solar Energy Utilization II*, vol. 85, pp. 39-46, (1976).

Fan et al., "Transparent Heat Mirrors for Solar Energy Applications", *Applied Optics*, vol. 15, No. 4, pp. 1012-1017, Apr. 1976.

Fan et al., "Transparent Heat Mirror Films of $TiO_2$-/Ag/$TiO_2$ for Solar Energy Collection and Radiation Insulation", *Applied Physics Letters*, vol. 25, No. 12, pp. 693-695, Dec. 1974.

Lighting Design & Application, vol. 9, No. 6, pp. 7 and 8, Jun. 1979.

*Primary Examiner*—James R. Hoffman
*Attorney, Agent, or Firm*—W. D. Palmer

[57] ABSTRACT

Energy-conserving incandescent lamp wherein the envelope has provided on the interior surface thereof a very efficient and economically applied heat mirror which is highly transmissive for visible radiations and highly reflective for infrared radiations, thereby to enhance the conversion of electric energy to visible energy. The heat-mirror coating comprises a two layer Ag/$TiO_2$ or a three layer $TiO_2$/Ag/$TiO_2$ coating of predetermined thickness. The three layer coating is formed by first applying to the envelope interior surface a thin layer of clear aliphatic alcohol solution having contained therein partially hydrolyzed metallic alkoxide which substantially comprises titanium alkoxide, and which solution contains at most only a limited amount of selected mineral acid. The applied clear solution layer is heat treated to convert same to a thin continuous layer substantially comprising titania. A thin silver layer is applied over the first applied titania coating, preferably by vacuum metallizing, and a second thin layer of solution containing the partially hydrolyzed metallic alkoxide which substantially comprises titanium alkoxide is applied over the silver layer. Thereafter the applied second layer is heat treated to convert same to titania, with the heat treating temperatures and atmospheres controlled so as not to affect the applied silver layer. The two layer coating is applied by omitting the first $TiO_2$ coating step.

9 Claims, 8 Drawing Figures

METHOD OF FABRICATING HEAT MIRROR FOR INCANDESCENT LAMP ENVELOPE

This is a continuation-in-part of application Ser. No. 931,346, filed Aug. 8, 1978, by Bulent E. Yoldas, the present applicant, and owned by the present assignee, now abandoned and refiled on Aug. 10, 1979, as Ser. No. 065,706, which discloses a method for forming anti-reflective films wherein specific relative amounts of metallic alkoxides, alcohol and water are reacted along with some mineral acid to produce polymerized clear solutions. These solutions are applied to a predetermined thickness on the substrate to be coated, such as a silicon wafer as used in a solar cell. After the coating material is applied, it is heat treated and the resulting coated wafer has substantially decreased reflectivity for the energizing radiations for the solar cell. The index of refraction of the optical oxide films deposited by this method, such as that of $TiO_2$, can be varied.

BACKGROUND OF THE INVENTION

This invention relates to a method for fabricating a heat mirror for incandescent lamp envelopes and the resulting product and, more particularly, to an improved and economical method for applying $Ag/TiO_2$ and $TiO_2/Ag/TiO_2$ heat mirrors for an incandescent lamp envelope.

The use of heat mirror filters as an envelope coating for incandescent lamps is described in U.S. Pat. No. 4,017,758 dated Apr. 12, 1977 to Almer. The particular filter described is a heavily doped metal oxide filter which has an interference filter coated thereover. More particularly, the doped metal oxide filter is tin-doped indium oxide. In the operation of such a lamp, infrared radiations emitted by the filament are reflected back toward the filament to contribute to filament heating, while visible radiations are passed through the filter, with a resulting improvement in the efficiency of conversion of electric energy into visible light.

The use of tin-doped indium oxide films for use as heat mirrors for solar energy utilization and the use of titania-silver-titania heat mirrors for solar energy utilization are disclosed in Society of Photo-Optical Instrumentation Engineers, Volume 85, pages 39–46 (1977), article by John C. Fan. A similar disclosure is set forth in Applied Optics, Volume 15, No. 4 (April 1976) pages 1012–1017, article by Fan et al.

Transparent heat mirrors of titania/silver/titania for solar energy collection of radiations are described in Applied Physics Letters, Volume 25, No. 12, 15 December 1974, pages 693–695, article by Fan et al. The physical design considerations for such heat mirrors are discussed in detail in these references. Whenever titania is utilized as a heat mirror film constituent, it is disclosed as being deposited with an RF sputtering technique.

An incandescent lamp wherein the envelope is provided with a multi-layer titania/silver/titania heat mirror is disclosed in Lighting Design & Application, Volume 9, No. 6, June, 1979, pages 7 and 8. Such a lamp is described in greater detail in U.S. Pat. No. 4,160,929, dated July 10, 1979 to Thorington et al. This patent indicates that the coating layers can be applied by other than RF sputtering, such as dipping, spraying, vapor deposition, chemical deposition, etc., but no details are given.

U.S. Pat. No. 2,689,858 dated Sept. 21, 1954, to Boyd discloses organic solvent soluble polymers of tetraorgano derivatives of orthotitanic acid. These are prepared by reacting alkyl titanates with a small amount of water to produce a haze-free polymer. These polymers have utility as modifiers for condensation resins.

U.S. Pat. No. 3,460,956 dated Aug. 12, 1969 to Dahle discloses the formation of thin titania coatings from clear alcohol-water solutions which are modified with lactic acid or nitric acid. In the case of nitric acid, the concentration is at least 0.5 mole acid per mole of tetraalkyl titanate placed into the solution.

U.S. Pat. No. 2,768,909 dated Oct. 20, 1956 to Halsam discloses applying tetraalkyl titanate to a substrate and then hydrolyzing same from the moisture in the atmosphere in order to produce a thin film which in some cases can be transparent. A similar technique has been used to coat an incandescent lamp envelope, as disclosed in British Pat. No. 703,127, published Jan. 27, 1954.

U.S. Pat. No. 3,094,436 dated June 18, 1963 to Schroder discloses depositing on a substrate partially hydrolyzed organic titanic and/or silicic acid esters in an alcohol vehicle, which on heat treatment convert to transparent reflection-reducing film coatings.

SUMMARY OF THE INVENTION

There is provided an economical method of applying a heat mirror, which is transmissive for visible radiations and reflective for infrared radiations, to the interior surface of a regularly conformed, hollow, thin-walled, vitreous, light-transmitting member which is intended for use as an envelope for an incandescent light source. In accordance with one embodiment of this method, there is applied to the interior surface of the envelope, to a substantially uniform predetermined thickness, a clear solution having contained therein partially hydrolyzed metallic alkoxide which in the metallic alkoxide form prior to hydrolyzation is expressed as $M(OR)_n$, wherein M at least substantially comprises titanium, R is alkyl with from 1 to 6 carbon atoms, and n is the valence of M. The total reacted and unreacted water in the solution is present in amount of from 0.6 mole to 8 moles per mole of the metallic alkoxide. The solution solvent is liquid aliphatic alcohol present in amount to provide a solutions solid content, expressed as equivalent metallic oxide, of from about 0.1% to about 5% by weight. As an optional constituent which may be used, the solution is acidified with at least one of hydrochloric, nitric and perchloric acid in amount of up to about 0.3 mole per mole of metallic alkoxide.

The envelope and the first applied solution are then heated to a temperature of from about 300° C. to about 600° C. but not exceeding the strain point for the envelope for a sufficient period of time to convert the applied clear solution to an adherent thin continuous metallic oxide layer. There is then applied over the first applied metallic oxide layer a thin continuous silver layer of predetermined thickness sufficient to be substantially transmissive for visible radiations and substantially reflective for infrared radiations. A vacuum metallizing process is preferred for applying the silver layer. There is then applied over the silver layer to a thin substantially uniform predetermined thickness a second clear solution as used to apply the first metallic oxide layer. The envelope and the second applied clear solution are then heated at a temperature of from about 300° C. to about 425° C. under conditions which are non-reactive for silver for a sufficient period of time to convert the second applied clear solution to an adherent, clear metallic oxide layer. There is also provided the improved electric incandescent lamp which incorporates an envelope prepared in accordance with the foregoing method.

In accordance with a second embodiment of this method, the first-applied titania coating is dispensed with and the silver layer is applied to the interior surface of the envelope. The overlaying titania coating is then applied as in the previous embodiment. There is also provided the improved electric incandescent lamp which incorporates an envelope prepared in accordance with this second method embodiment, as well as an incandescent lamp which incorporates a two-layer heat mirror, namely, a first silver layer with a titania overlay.

BRIEF DESCRIPTION OF THE DRAWINGS

For a better understanding of the invention, reference may be had to the preferred embodiment, exemplary of the invention, shown in the accompanying drawings, in which.

DESCRIPTION OF THE PREFERRED EMBODIMENTS

Figure 1:
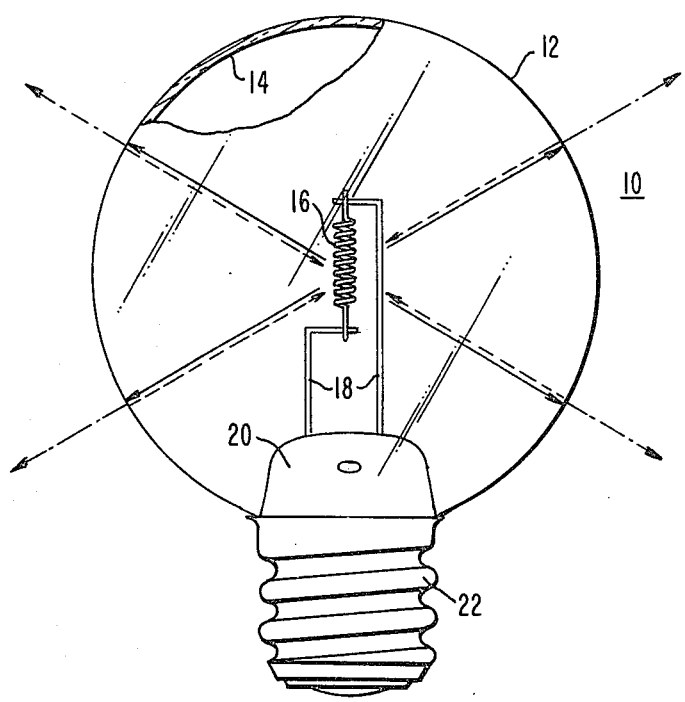
FIG. 1 is an elevational view, partly in section, of an energy-conserving incandescent lamp wherein one embodiment of a heat mirror formed in accordance with the present invention is provided on the inner surface of the envelope.
Figure 2:
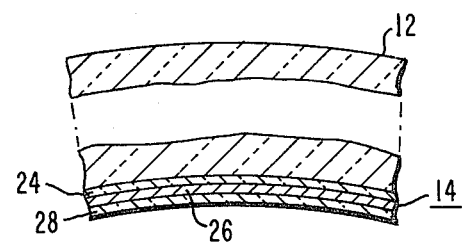
FIG. 2 is a greatly enlarged cross section of a fragment of the lamp envelope as shown in FIG. 1 illustrating the coated heat mirror.

With specific reference to the form of the invention illustrated in the drawings, the incandescent lamp 10 as shown in FIG. 1 comprises a sealed, regularly conformed, hollow, thin-walled, light-transmitting vitreous envelope 12 fabricated of glass such as the conventional soda-lime-silica soft glass. A heat mirror 14, which is shown in greatly enlarged form in FIG. 2, is carried on the interior surface of the envelope 12 and the heat mirror is operative to substantially transmit visible radiations and to substantially reflect infrared radiations. An incandescent filament means 16 of coiled or multiple-coiled configuration is operatively positioned within the envelope 12 so that infrared radiations emitted therefrom during lamp operation will be reflected by the heat mirror 14 to impinge upon the filament 16, thereby to enhance the conversion of electric energy to visible energy. In the embodiment as shown in FIG. 1, the envelope has a spherical configuration and the filament 16 is positioned proximate the center of the sphere. For purposes of illustration, the visible and infrared radiations emitted by the operating filament 16 are represented as solid lines, with the transmitted visible radiations represented as dot-dash lines, and the reflected infrared radiations represented as dashed lines. To complete the description of the lamp 10, the filament 16 is supported proximate the midpoint or center of the spherical envelope 12 by means of conventional lead-in suports 18 which are sealed through a conventional mount and stem-press arrangement 20, with a standard screw type base 22 affixed to the neck portion of the envelope 12.

The reflectance and transmittance of extremely thin films of silver is well known and is reported, for example, in "Optical Properties of Thin Solid Films" by O. S. Heavens, Academic Press Inc., New York, New York (1955), see pages 166–169 and particularly, the reflectance-transmittance characteristics shown in FIG. 6.10 at page 167. When silver is deposited as a thin continuous layer to a thickness of 180 Angstroms, for example, it will be substantially transmissive for visible radiations and substantially reflective for infrared radiations. It is also known to use thin films of various substantances for antireflection coatings such as described in "Physics of Thin Films" edited by Hass, Academic Press, New York, New York (1964), Volume 2, see pages 239–304. The use of combined titania-silver-titania films for solar energy collection and radiation insulation is described in the heretofore-referenced article in Applied Physics Letters, Volume 25, No. 12, 15 Dec. 1974. As described therein, using the calculated formulations of O. S. Heavens, Optical Properties of Thin Solid Films, Dover, New York, (1965), page 169, for optimum performance as a heat mirror, each of the films should have a thickness of approximately 180 Angstroms, as deposited on the glass substrate. As taught by this Applied Physics Letter article, the techniques used to deposit each of these films are RF sputtering, which is a relatively slow process and requires elaborate equipment. For example, as described in this article, to deposit the first titania film to a thickness of 180 Angstroms requires 7.5 minutes. In accordance with the present invention, as will be described hereinafter, the titania film or films can be simply and rapidly formed by applying a clear solution onto the substrate to be coated and then heating same to convert the solution to a thin, clear titania film of predetermined thickness.

The formed heat mirror coating is shown in greatly enlarged fragmentary form in FIG. 2 wherein the envelope 12 is formed of conventional soda-lime-silica glass having a thickness of 0.6 mm to 1.3 mm, for example. On the interior envelope surface is formed a first film 24 of titania having a thickness of 180 Angstroms, for example. Over the titania film 24 is formed a thin layer 26 of silver, also having a thickness of 180 Angstroms, for example. Over the silver layer is formed a second film 28 of titania which also has a thickness of 180 Angstroms, for example. As explained in the aforementioned Applied Physics Letters article, the differing refractive indexes of the titania and silver necessitate the thinner films which vary from the conventional quarter wavelength films.

Figure 3:
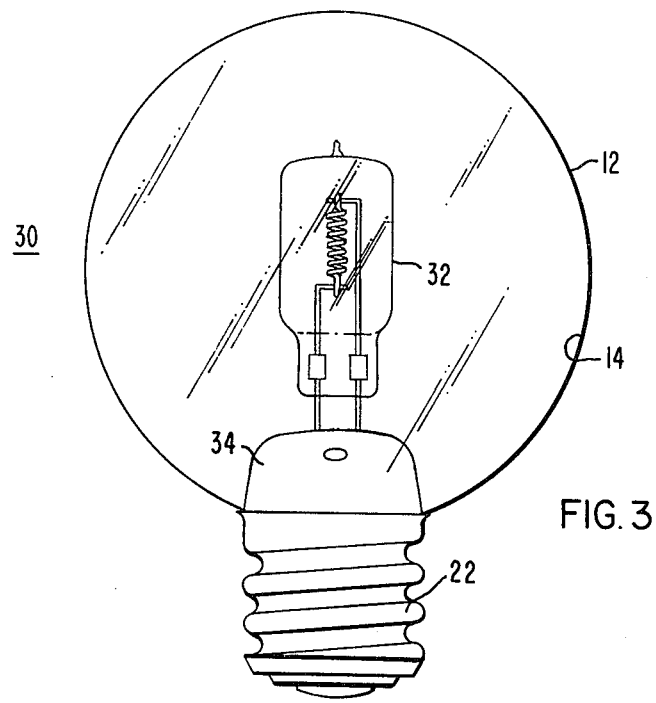
FIG. 3 is an elevation view, shown partly in section, of an incandescent lamp generally similar to that shown in FIG. 1 except that the incandescent source is of the quartz-halogen type enclosed within the energy-conserving outer envelope.

An alternative lamp embodiment 30 is shown in FIG. 3 wherein the incandescent source comprises a conventional miniature-type quartz halogen lamp 32 which is affixed to a conventional stem-press arrangement 34. In other respects, the lamp is conventional and the envelope 12 has a spherical configuration and carries the present heat-mirror coating 14, as described hereinbefore, on the interior surfaces. In such an embodiment, the outer envelope 12 can be evacuated if desired in order to minimize convection losses. As in the previous embodiment, a conventional base 22 is affixed to the neck of the envelope 12.

Figure 4:
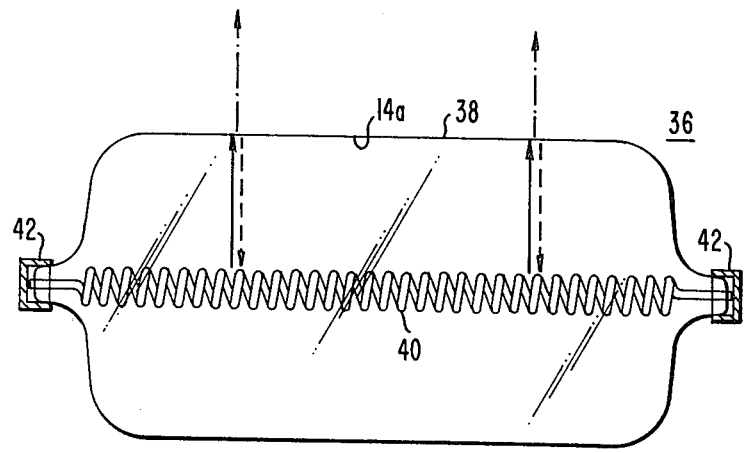
FIG. 4 is an elevational view of a different form of incandescent lamp wherein the envelope has a tubular configuration and the filament is coiled and elongated and the envelope carries on its interior surface a heat mirror which has been prepared in accordance with the present invention.

Another embodiment is shown in FIG. 4 wherein the lamp 36 has a spherical envelope 38 which carries the heat-mirror coating 14a, as described hereinbefore, on the interior surface. An elongated coiled incandescible filament 40 is positioned along the axis of the cylindrical envelope and connects to contact members 42 provided at either end of the envelope. Such a construction is generally similar to that shown in the heretofore referenced U.S. Pat. No. 4,017,758 and, if desired, the filament can be positioned within a much smaller envelope which forms a part of a quartz-halogen lamp such as described in this referenced patent.

To apply the heat-mirror coating 14 or 14a as described hereinbefore, there is first applied to the interior surface of the lamp envelope, to a substantially uniform predetermined thickness, a clear solution having contained therein partially hydrolyzed metallic alkoxide which in the metallic alkoxide form prior to hydrolyzation is expressed as $M(OR)_n$, wherein M at least substantially comprises titanium, R is alkyl with from 1 to 6 carbon atoms and n is the valence of M. Total reacted and unreacted water in this solution is present in amount of from 0.6 mole to 8 moles per mole of the metallic alkoxide, and the solution solvent is liquid aliphatic alcohol present in amount to provide a solution solids content, expressed as equivalent metallic oxide, from about 0.1% to about 3% by weight. In some cases where lighter alcohols are used as the solvent, such as ethanol, there may be some tendency for the solution to appear cloudy and this is readily removed by adding to the solution at least one of hydrochloric, nitric and perchloric acid in amount of up to about 0.3 mole per mole of metallic alkoxide. This acid addition is thus an optional constituent.

The prepared clear solution is poured or sprayed into the envelope to thoroughly wet same and excess applied solution is allowed to drain for approximately one-half minute. This will provide the applied solution with a substantially uniform predetermined thickness of about 350 Angstroms for a one percent equivalent titania-containing solution. The envelope is then heated to a temperature of from about 300° C. to about 600° C., but not exceeding the strain point of the envelope, for a sufficient period of time to convert the applied clear solution to an adherent, continuous, metallic oxide layer at which point the thickness of the coating is reduced to about one-half of the initial coating. As a specific example, for a typical soda-lime-silica glass, the strain point is about 478° C. so that this will normally constitute the upper limit for the heating temperature for the applied solution. As is well known, the strain point of glass is that temperature at which the glass has a viscosity of $10^{14.6}$ poises.

After the first titania layer is applied, there is applied thereover a thin continuous silver layer of predetermined thickness sufficient to be substantially transmissive for visible radiations and substantially reflective for infrared radiations. The preferred method for depositing the silver layer is vacuum metallizing. Thereafter, there is applied over the silver layer to a thin, substantially uniform, predetermined thickness a second clear alkoxide solution as used to apply the first-applied metallic oxide layer. The applied second solution and envelope are then heated to a temperature of from about 300° C. to about 425° C. under conditions which are non-reactive for silver for a sufficient period of time to convert the second applied clear solution to an adherent clear metallic oxide layer. As an example, suitable heating environments which are non-reactive for the silver are vacuum or an inert gas and the upper temperature limitation of about 425° C. prevents reaction with the silver layer.

Considering a specific example, to prepare a 1% by weight solution based on the equivalent titania content, 22.8 grams (0.1 mole) of $Ti(OC_2H_5)_4$ has added thereto 773 grams secondary butyl alcohol and 3.6 grams water. To this is added a 70% nitric acid solution in amount of 0.2 gram. This will provide 800 grams of solution containing the equivalent of 8 grams of titania. The foregoing solution is poured into a bulb and poured out under room temperature conditions and the bulb is allowed to drain for approximately one-half minute, which will leave a substantially uniform film of solution on the interior surface of the bulb of a thickness of about 300 Angstroms. The bulb is then baked in air at a temperature of approximately 450° C. for 1 to 5 minutes, with 3 minutes being a specific example. This converts the applied titanium ethoxide to a thin continuous film of titania having a thickness of approximately 180 Angstroms.

There is then applied over the deposited titania coating a thin silver layer having a thickness of approximately 180 Angstroms and the thickness of the silver is readily controlled with conventional vacuum metallizing equipment.

The same solution as used to apply the first titania coating is again poured into the bulb and poured out with the bulb allowed to drain for approximately one-half minute. The bulb is then heated to approximately 375° C. under vacuum conditions for approximately 5 minutes which will provide an applied coating of titania having a thickness of approximately 180 Angstroms.

Figure 5:
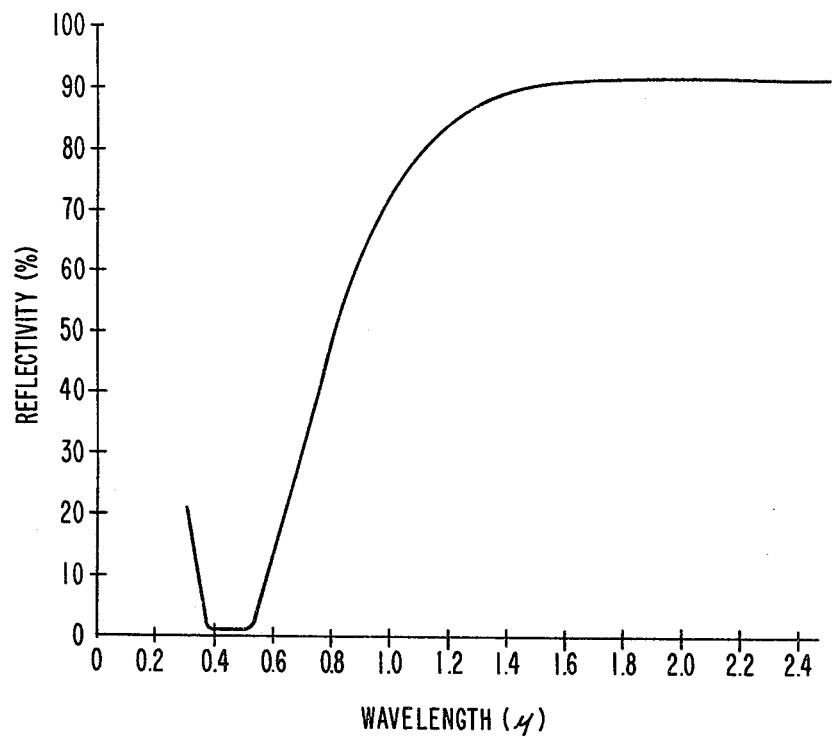
FIG. 5 is a graph of reflectivity vs. wavelength for a heat-mirror coating applied in accordance with the present invention to a glass plate.
Figure 6:
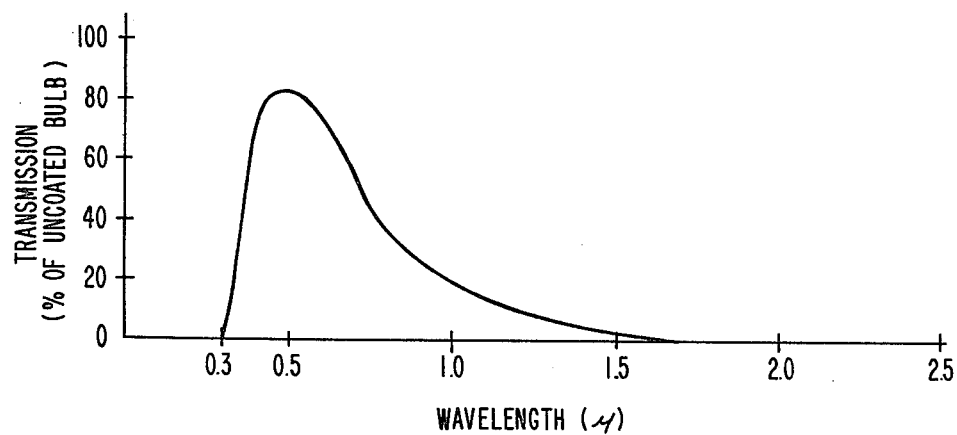
FIG. 6 is a graph of transmission vs. wavelength for a bulb such as shown in FIG. 1 coated with a heat mirror applied in accordance with the present invention.

The performance of the foregoing heat mirror coatings is illustrated in FIGS. 5 and 6, wherein FIG. 5 plots reflectivity versus wavelength for a 180Å $TiO_2$, 180Å Ag, 180Å $TiO_2$ coating deposited on a flat glass substrate. Within a substantial portion of the visible range, the reflectivity is less than 2% and in the infrared range, the reflectivity rises rapidly to over 90%.

In FIG. 6 is plotted transmission versus wavelength for the specific coated bulb as described hereinbefore, with the measured transmission for an uncoated bulb used as a standard. For this embodiment, at 0.5 micron (500 nm) the transmission of the coated bulb is approximately 82% of that of the uncoated bulb and in the infrared range of the spectrum, the transmission rapidly drops and approaches zero at wavelengths longer than 1.5 microns (1500 nm).

The titania layer can readily be modified to incorporate other metal oxides by virtue of the method of deposition and as disclosed in the referenced copending application Ser. No. 065,706, filed Aug. 10, 1979. This is readily accomplished by substituting up to 25 mole percent silicon ethoxide for the titanium ethoxide in the foregoing specific example so that the composite index of refraction can be carefully controlled for best results. Such mixed oxide layers normally cannot be formed with the usual RF sputtering deposition technique. As a specific example, the solution can be varied to incorporate therein titanium tetraethoxide and silicon tetraethoxide in the relative molar ratios of 90:10. Minor amounts of other metallic ethoxides can also be utilized so that the other metallic oxide will appear in the final coating, an example being tantalum ethoxide, Ta-$(OC_2H_5)_5$.

The thickness of the dielectric material layers, 24 and 28 as shown in FIG. 2, can be readily varied by varying the solids content of the solution or the solution viscosity by various degrees of hydrolysis or using various alcohols, with higher solids contents and higher viscosities producing thicker coatings. The viscosity can readily be controlled by selecting the alcohol with the lower alcohols providing a reduced viscosity. While the foregoing example has considered titanium tetraethoxide, any other alkoxide may be substituted therefor with the alkyl groups having from 1 to 6 carbon atoms. Alternatively, different alkoxides can be mixed and used in the same coating solution, an example being equal gram mole parts of titanium tetraethoxide and titanium butoxide.

While the solution solvent is selected to be liquid aliphatic alcohol, various alcohols can be mixed, in order to vary the viscosity of the solutions and thus the thickness of the deposited coating. An example of such a mixture is equal parts by weight of ethanol and secondary butanol.

In its preferred form, the coating solution is so compounded that the total reacted and unreacted water in the solution is present in amount of from about 1.5 moles to about 2.5 moles per mole of metallic alkoxide in the solution. The preferred solids content, expressed as equivalent metallic oxide, is from about 1% to about 2% by weight, and the solution preferably is acidified with at least one of hydrochloric, nitric and perchloric acid in amount of from about 0.02 to about 0.03 mole per mole of metallic alkoxide in the solution. With heavier alcohols such as butanol, at low solid concentrations, e.g. 1% or less equivalent $TiO_2$, acids are not required to produce clear solutions.

In the preferred method for applying the first coating layer 24, the applied solution is heated to a temperature of from about 325° C. to about 550° C., but not exceeding the strain point of the glass envelope material. In the preferred method for applying the second titania coating 28 over the silver coating 26, the applied solution is heated to a temperature of from about 325° C. to about 375° C. to minimize any tendency for the applied silver layer 26 to diffuse. It is found that above about 425° C., integrity of such silver layers is readily destroyed. Acid concentrations in excess of about 0.3 mole per mole of metallic alkoxide in the second metallic alkoxide coating solutions can present problems with respect to reactions with the previously applied silver coatings.

While the silver layer 26 as shown in FIG. 2 is preferably applied with a vacuum metallizing techique, this silver layer can also be applied with RF sputtering or it can be applied from a solution.

The present method of applying the dielectric layers with a solution application technique particularly lends itself to mass production and an economical product since the solutions can be applied with a simple dipping, spray or flush coating technique inside or outside of the bulb, and the heat treatment can be conducted on an automated basis. In addition, high-speed vacuum metallizing equipments are readily available for production application of the silver layers.

The foregoing specific example of a heat mirror coating has considered three layers each having a thickness of approximately 180 Angstroms. For varying dielectric constants and varying materials, it may be desirable to vary this thickness and this can readily be accomplished. In the usual case, however, the thickness of each of the titania layers will fall within the range of from 100 to 400 Angstroms and this coating thickness can readily be controlled on a production basis in the manner as described hereinbefore. The thickness of the silver layer can also be varied.

The described embodiment of the present heat mirror essentially comprises a three-layer structure of titania-silver-titania. The solution method of coating deposition is readily adapted for applying additional coating layers, such as a layer of silicon dioxide or magnesium fluoride, for example, in order to modify the reflection-transmission characteristics of the heat mirror. As a specific example, a very thin coating of silicon dioxide can be deposited over the second formed titania layer utilizing the silicon tetraethoxide deposition, followed by heat treatment.

As a possible alternative embodiment, in the case of a spherical envelope, a metallic shield can be carried on the stem portion of the mount 20 such as described in aforementioned U.S. Pat. No. 4,160,929.

Figure 7:
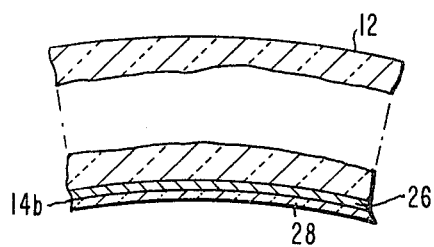
FIG. 7 is a greatly enlarged cross section of a fragment of a lamp envelope generally as shown in FIG. 1, but illustrating an alternative embodiment wherein the heat mirror is formed as a two-layer silver-titania mirror.

As an alternative embodiment for a heat mirror, it has been found that the first titania coating 24, as shown in FIG. 2, can be dispensed with and the silver layer applied directly onto the inner surface of the incandescent lamp envelope. Such an alternative coating 14b is shown in FIG. 7 wherein the envelope member 12 is provided with a spherical configuration and the incandescent lamp is generally fabricated in accordance with the construction as shown in FIG. 1 and as described hereinbefore. In accordance with this embodiment as shown in FIG. 7, the silver layer 26 is deposited as previously described, preferably utilizing a vacuum metallizing technique, to a thickness as previously described. This will provide a silver layer which is substantially transmissive for visible radiations and substantially reflective for infrared radiations. As a specific example, silver deposited to a thickness of approximately 180 Angstroms will provide this result. Over the silver layer 26 is applied the clear solution in a manner identical to the previously described second titania coating, with the subsequent heat treatment being identical to that which was used for the previously described second applied titania coating. The resulting titania layer 28, as shown in FIG. 7, thus can be identical to the second titania layer 28, as shown in FIG. 2. The advantage of such a modified heat mirror 14b is that one processing step is eliminated and, in addition, the performance of the resulting heat mirror is at least equivalent to the performance of the three-layer mirror, as shown in FIG. 2 and as previously described.

Figure 8:
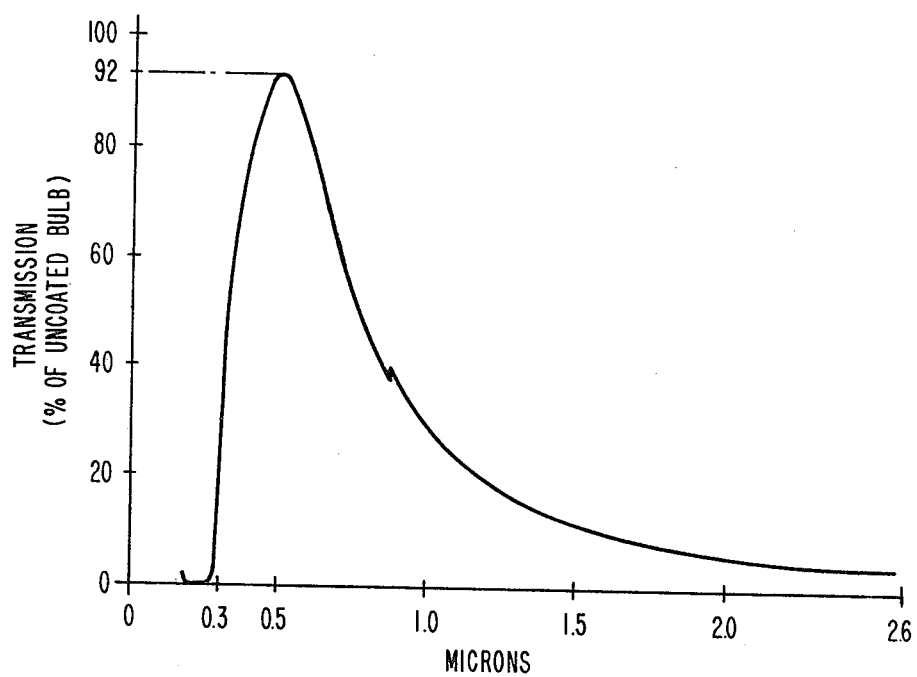
FIG. 8 is a graph of transmission vs. wavelength for a heat-mirror formed as a two-layer coating, as shown in FIG. 7.

In FIG. 8 is shown a graph of transmission versus wavelength for a spherical incandescent bulb which is shown in fragmentary form in FIG. 7. The maximum transmission in the visible range for such a coating is approximately 92 percent of the transmission of an uncoated bulb which is used as the standard or control. At a wavelength of 1.5 microns, the transmission of the coated bulb is approximately 12 percent of that of the uncoated bulb which is used as the standard.

The overlying titania coating 28, as shown in FIG. 7, can be applied in the same manner as the second titania coating 28 which is shown in FIG. 2 and which is described in detail hereinbefore. Reference is made to the previous description for details including process parameters. In its preferred form the titania coating 28 will have a thickness of from about 100 Angstroms to about 400 Angstroms.

The present process permits the index of refraction of the film or films comprising titania to be varied and this enables the resulting titania coating or coatings to have an index of refraction which is tailored for improved transmission of the visible radiations and improved reflection in the infrared, including the near infrared. For example, while titania is normally regarded as having an index of refraction of about 2.6, the present process permits the index to be varied, either by including other metal oxides or by varying the process parameters. For example, the lower the heating temperature for the applied titania alkoxide coating solution, the lower the index and if the heating is conducted in vacuum, the index of refraction of the coating will normally be increased. This ability to vary and control the index of refraction makes possible the fabrication of a two-layer silver-titania heat mirror having the transmission characteristics as shown in FIG. 8.

I claim:

1. The method of applying a heat mirror which is transmissive for visible radiations and reflective for infrared radiations to the interior surface of a regularly conformed hollow thin-walled vitreous light-transmitting member intended for use as an envelope for an incandescent light source, which method comprises:
   a. applying to the interior surface of said envelope, to a substantially uniform predetermined thickness, a clear solution having contained therein partially hydrolyzed metallic alkoxide which in the metallic alkoxide form prior to hydrolyzation is expressed as $M(OR)_n$, wherein M at least substantially comprises titanium, R is alkyl with from 1 to 6 carbon atoms, and n is the valence of M; total reacted and unreacted water in said solution being present in amount of from 0.6 mole to 8 moles per mole of said metallic alkoxide; the solution solvent being liquid aliphatic alcohol present in amount to provide a solution solids content, expressed as equivalent metallic oxide, of from about 0.1% to about 3% by weight; and as an optional constituent, said solution is acidified with at least one of hydrochloric, nitric and perchloric acid in amount of up to about 0.3 mole per mole of said metallic alkoxide;
   b. heating said envelope and first applied solution to a temperature of from about 300° C. to about 600° C. but not exceeding the strain point of said envelope for a sufficient period of time to convert said applied clear solution to an adherent thin continuous metallic oxide layer;
   c. applying over said first applied metallic oxide layer a thin continuous silver layer of predetermined thickness sufficient to be substantially transmissive for visible radiations and substantially reflective for infrared radiations;
   d. applying over the applied silver layer to a thin substantially uniform predetermined thickness a second clear solution as used to apply said first-applied metallic oxide layer; and
   e. heating said envelope and applied second clear solution to a temperature of from about 300° C. to about 425° C. under conditions which are non-reactive for silver for a sufficient period of time to convert said second applied clear solution to an adherent clear metallic oxide layer.

2. The method of applying a heat mirror which is transmissive for visible radiations and reflective for infrared radiations to the interior surface of a regularly conformed hollow thin-walled vitreous light-transmitting member intended for use as an envelope for an incandescent light source, which method comprises:
   a. applying to the interior surface of said envelope, to a substantially uniform predetermined thickness, a clear solution having dissolved therein partially hydrolyzed titanium alkoxide which in the alkoxide form prior to hydrolyzation is expressed as $Ti(OR)_4$, wherein R is alkyl with from 1 to 6 carbon atoms; total water in said solution is present in amount of from about 1.5 moles to about 2.5 moles per mole of said titanium alkoxide; the solution solvent being liquid aliphatic alcohol present in amount to provide a solution solids content, expressed as equivalent titanium oxide, of from about 1% to about 2% by weight; and said solution is acidified with at least one of hydrochloric, nitric and perchloric acid in amount of from about 0.02 to about 0.03 mole per mole of titanium alkoxide;
   b. heating said envelope and first applied solution to a temperature of from about 325° C. to about 550° C. but not exceeding the strain point of said envelope for a sufficient period of time to convert said applied clear solution to an adherent thin continuous titanium oxide layer;
   c. vacuum metalizing over said first applied titanium oxide layer a thin continuous silver layer of predetermined thickness sufficient to be substantially transmissive for visible radiations and substantially reflective for infrared radiations;
   d. applying over the applied silver layer to a thin substantially uniform predetermined thickness a second clear solution as used to apply said first-applied titanium oxide layer; and
   e. heating said envelope and applied second clear solution to a temperature of from about 325° C. to about 375° C. under conditions which are non-reactive for silver for a sufficient period of time to convert said second applied clear solution to an adherent clear titanium oxide layer.

3. The method as specified in claim 2, wherein said titanium alkoxide is titanium ethoxide, said solution solvent is sec butyl alcohol, the solution solids content expressed as equivalent titanium oxide is about 1% by weight, and said solution is acidified with nitric acid.

4. The method as specified in claim 3, wherein said first applied titanium oxide layer and said second aplied titanium oxide layer each have a thickness in the range of from 100 to 400 Angstroms.

5. The method of applying a heat mirror which is transmissive for visible radiations and reflective for infrared radiations to the interior surface of a regularly conformed hollow thin-walled vitreous light-transmitting member intended for use as an envelope for an incandescent light source, which method comprises:
   a. applying contiguous with the interior surface of said vitreous member a thin continuous silver layer of predetermined thickness sufficient to be substantially transmissive for visible radiations and substantially reflective for infrared radiations;

b. applying over the applied silver layer to a substantially uniform predetermined thickness, a clear solution having contained therein partially hydrolyzed metallic alkoxide which in the metallic alkoxide form prior to hydrolyzation is expressed as $M(OR)_n$, wherein M at least substantially comprises titanium, R is alkyl with from 1 to 6 carbon atoms, and n is the valence of M; total reacted and unreacted water in said solution being present in amount of from 0.6 mole to 8 moles per mole of said metallic alkoxide; the solution solvent being liquid aliphatic alcohol present in amount to provide a solution solids content, expressed as equivalent metallic oxide, of from about 0.1% to about 3% by weight; and as an optional constituent, said solution is acidified with at least one of hydrochloric, nitric and perchloric acid in amount of up to about 0.3 mole per mole of said metallic alkoxide; and c. heating said envelope and applied clear solution to a temperature of from about 300° C. to about 425° C. under conditions which are non-reactive for silver for a sufficient period of time to convert said second applied clear solution to an adherent clear metallic oxide layer.

6. The method of applying a heat mirror which transmissive for visible radiations and reflective for infrared radiations to the interior surface of a regularly conformed hollow thin-walled vitreous light-transmitting member intended for use as an envelope for an incandescent light source, which method comprises:

a. applying onto the interior surface of said vitreous member a thin continuous silver layer of predetermined thickness sufficient to be substantially transmissive for visible radiations and substantially reflective for infrared radiations;

b. applying over the applied silver layer to a substantially uniform predetermined thickness, a clear solution having dissolved therein partially hydrolyzed titanium alkoxide which in the alkoxide form prior to hydrolyzation is expressed as $Ti(OR)_4$, wherein R is alkyl with from 1 to 6 carbon atoms; total water in said solution is present in amount of from about 1.5 moles to about 2.5 moles per mole of said titanium alkoxide; the solution solvent being liquid aliphatic alcohol present in amount to provide a solution solids content, expressed as equivalent titanium oxide, of from about 1% to about 2% by weight; and said solution is acidified with at least one of hydrochloric, nitric and perchloric acid in amount of from about 0.02 to about 0.03 mole per mole of titanium alkoxide; and c. heating said envelope and applied clear solution to a temperature of from about 325° C. to about 375° C. under conditions which are non-reactive for silver for a sufficient period of time to convert said second applied clear solution to an adherent clear titanium oxide layer.

7. The method as specified in claim 6, wherein said silver layer is applied by vacuum metalizing same onto the interior surface of said vitreous member.

8. The method as specified in claim 7, wherein said titanium alkoxide is titanium ethoxide, said solution solvent is sec butyl alcohol, the solution solids content expressed as equivalent titanium oxide is about 1% by weight, and said solution is acidified with nitric acid.

9. The method as specified in claim 8, wherein said applied titanium oxide layer has a thickness in the range of from 100 to 400 Angstroms.

* * * * *